US006575909B2

(12) United States Patent
De Jong et al.

(10) Patent No.: US 6,575,909 B2
(45) Date of Patent: Jun. 10, 2003

(54) ULTRASOUND PROBE HAVING TRANSDUCER ELEMENTS WITH DIFFERENT FREQUENCY CENTERS

(75) Inventors: Nicolaas De Jong, Krimpen Aan Den Ijssel (NL); Robert Jan Smallenburg, Gouda (NL); Rudi Frans Mastenbroek, Leiden (NL)

(73) Assignee: Oldelft B.V., Delft (NL)

( * ) Notice: Subject to any disclaimer, the term of this patent is extended or adjusted under 35 U.S.C. 154(b) by 0 days.

(21) Appl. No.: 09/757,867

(22) Filed: Jan. 9, 2001

(65) Prior Publication Data

US 2001/0021809 A1 Sep. 13, 2001

(30) Foreign Application Priority Data

Jan. 25, 2000 (NL) .......................................... 1014175

(51) Int. Cl.[7] .............................................. A61B 8/14
(52) U.S. Cl. ...................................... 600/458; 600/459
(58) Field of Search ............................... 600/437, 443, 600/447, 458, 459; 310/340, 342, 358; 367/11; 29/25.35

(56) References Cited

U.S. PATENT DOCUMENTS 5,099,459 A * 3/1992 Smith ........................ 29/25.35
5,420,429 A 5/1995 Eberhard et al.
5,509,417 A 4/1996 Dias et al.
5,906,580 A 5/1999 Kline-Schoder et al.
6,117,082 A * 9/2000 Bradley et al. ............ 600/447

FOREIGN PATENT DOCUMENTS

| | | |
|---|---|---|
| JP | 508032 | 1/1993 |
| JP | 509745 | 1/1993 |
| WO | WO 92/18164 | 10/1992 |
| WO | WO 94/08627 | 4/1994 |
| WO | WO 96/15814 | 5/1996 |
| WO | WO 99/35967 | 7/1999 |

OTHER PUBLICATIONS

Thomas P. Stephens, "Ultrasound Transducer With Wider Range Of Focus And Penetration", Research Disclosure, Great Britain, Industrial Opportunities LTD. Havant, No. 399, Jul. 1, 1997.
Dutch Search Report.

* cited by examiner

*Primary Examiner*—Marvin M. Lateef
*Assistant Examiner*—Ali M. Imam
(74) *Attorney, Agent, or Firm*—Altera Law Group, LLC

(57) ABSTRACT

Described herein is an ultrasound probe for ultrasound imaging using contrast enhancing agents and including two interleaved arrays of transducer elements. Each array has a longitudinal dimension along which transducer elements are placed. One interleaved array includes transducer elements having a lower center frequency. Another interleaved array includes transducer elements having a higher center frequency. The transducer elements are provided on interfitting support members. A length of the transducer elements of one array is larger than a corresponding length of the transducer elements of the other array.

7 Claims, 6 Drawing Sheets

ULTRASOUND PROBE HAVING TRANSDUCER ELEMENTS WITH DIFFERENT FREQUENCY CENTERS

The invention relates to an ultrasound probe for ultrasound imaging using contrast enhancing agents and comprising two interleaved arrays of transducer elements, each of said arrays having a longitudinal dimension along which said transducer elements are placed side by side, a first one of said interleaved arrays comprising transducer elements having a lower center frequency and a second one of said interleaved arrays comprising transducer elements having a higher center frequency.

Such a probe is described in international patent application no. WO99/35967 and is used for ultrasound imaging and more particularly in a multipulse and enhancement strategy for ultrasound imaging of an object containing an ultrasound contrast enhancing imaging agent.

Ultrasound contrast agents can be introduced into the body to reflect or absorb ultrasound energy, or to resonate when exposed to such energy, and thereby provide an enhanced image of a part of the body. Examples of such contrast agents, in the form of hollow microcapsules, are given in Japanese patent applications nos. 508032/1992 and 509745/1994 and in PCT/GB95/02673 (WO96/15814). Such agents are injected into the patient's bloodstream and then the patient is subjected to ultrasound radiation.

An ultrasound sequence may comprise a multiple sequence comprising a first pulse burst at a first frequency and low amplitude followed by a second pulse burst at a second frequency and relatively higher amplitude. This second pulse is of sufficient magnitude to induce power enhanced scattering, as defined, in a region of interest. This is then further followed by a third pulse burst of a third frequency and lower amplitude.

Power enhanced scattering is defined as providing an acoustic pulse at an amplitude at least sufficient to cause a change in the acoustic properties of the region of interest to, for example, cause bubbles to be released from the microcapsules.

A known method of producing an ultrasound image of an object containing an ultrasonic contrast imaging agent comprises subjecting the object to a first pulse burst of a first sequency and first power, subjecting the object to a second pulse burst of a second frequency in combination with a second power for optimal bubble release and subjecting the object to a third pulse burst of a third frequency and third power, obtaining a first image of the object as a result of the first pulse burst, obtaining a second image of the object as a result of the third pulse burst and comparing the first and second images to obtain a final enhanced image.

Preferably said first power is a low power relative to said second power which is a high power and said third power is a low power relative to said second power.

Preferably the first and third pulse bursts are at a frequency higher than that of the second pulse bursts, but alternatively the first and third pulse burst may be at a frequency lower than that of the second pulse burst.

Preferably the first and third pulse bursts are identical or have a defined and known relationship.

Preferably the first and third pulse bursts comprise a relatively lower number of cycles than the second pulse burst.

The first and third pulse bursts may comprise a single cycle.

The second pulse burst comprises a plurality of cycles.

Preferably the time between the first and third pulse bursts is less than 100 μs.

The third pulse birst may be combined with or overlap with the second pulse bursts. Any image pulse obtained from the third pulse burst can be filtered out from any interference from the second pulse bursts by virtue of the difference in frequencies.

In the imaging method a first image is obtained during the first pulse burst and a second image is obtained during the third pulse burst. The second higher amplitude pulse burst comprises a release burst for release of bubbles from a suitable agent such as Quantison.

Suitable microcapsules include those disclosed as "QUANTISON"™ microcapsules by Andaris Limited, and described in WO92/18164 (U.S. Pat. No. 5,518,709), WO94/08627 and WO96/15814 (U.S. Ser. No. 08/676,344 filed Jul. 19, 1996). The microcapsules are made by sparedrying a solution of serum albumin to form hollow microcapsules generally of diameter 1 to 10 μm; for example 90% may have a diameter of 1.0 to 9.0 μm or 1 to 6.0 μm, as measured in a Coulter Counter Multmizer II. However, any gas containing microcapsule, microsphere or microparticle which releases the gas on irridation with a non-physiologically harmful dose of ultrasound may be used in the methods of the invention.

In an enhancement sequence the first and second images obtained during the first and third pulse bursts are compared with each other to provide a combined improved image, for example by subtractive decorrelation.

A further description of the prior art will now be given with reference to some of the accompanying drawings in which.

Figure 1:
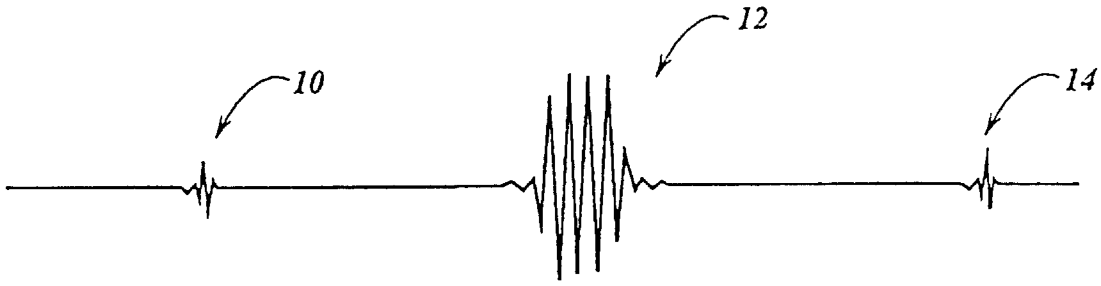
FIG. 1 shows an exemplary pulse burst sequence.

With reference to FIG. 1, an exemplary multipulse sequence comprises a first pulse burst 10 at relatively low amplitude and a third pulse burst 14 also at relatively low amplitude, both pulse bursts being at relatively high frequency, e.g. 5 MHz and relatively fewer cycles compared to the second pulse burst. A preferred embodiment comprises a pulse that is shaped for maximum resolution on imaging. In the specific embodiment shown only one cycle is used.

The first and third pulse bursts are preferably identical but they may have a defined relationship and in this case the processing circuitry will compensate to provide a comparative image.

In between these pulse bursts is positioned a second pulse burst having a power selected for optimal bubble release. In the embodiment shown the second pulse burst is a relatively low frequency (e.g. 2 MHz) pulse burst having a greater amplitude. The second pulse burst also preferably has a greater number of cycles than the first pulse burst. Preferably the second pulse burst comprises a pulse burst that is optimal for gas bubble release. In a specific embodiment the pulse burst has four or more cycles.

The second pulse burst could, however, be of higher frequency, in which case the power (amplitude) of the second pulse burst could for some microcapsules be lower.

What is required is a pulse burst of such frequency and power for the microcapsules that bubble release occurs and this will depend on a number of factors, including the type of microcapsule, which factors will be known to the person skilled in the art.

In operation two images are taken, one on each of the first and third pulse bursts, and the second pulse burst is used to induce Power Enhanced Scattering (PES) of bubbles from microcapsules contained in the region of interest. The image taken during the first pulse burst is compared with that in the third pulse burst to obtain an enhanced comparative image.

Figure 2:
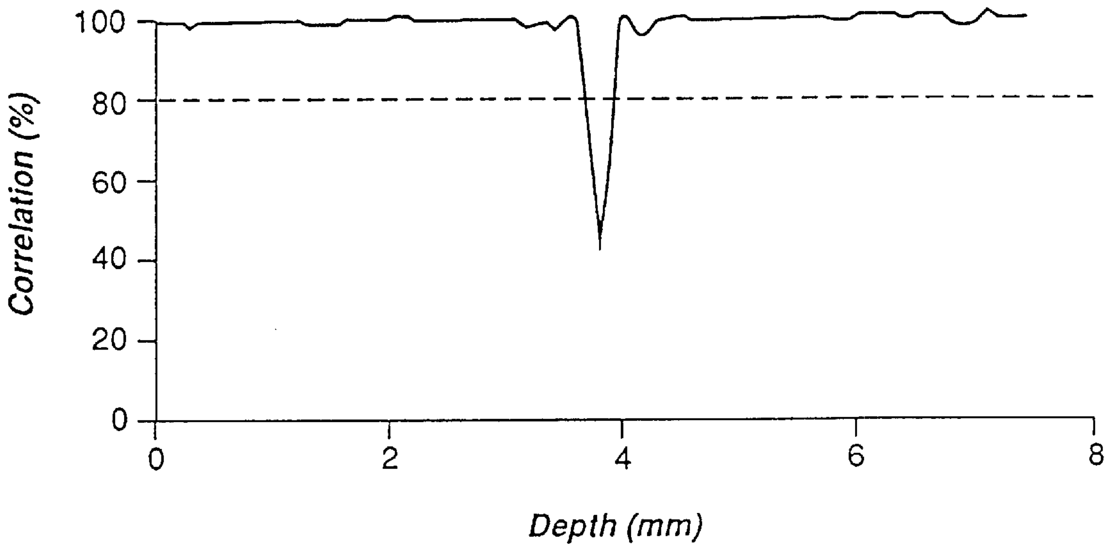
FIG. 2 shows a decorrelation profile obtained using the pulse burst sequence of FIG. 1.

FIG. 2 shows the comparison, in this case a substractive decorrelation obtained from the pulse sequence of FIG. 1 with thresholding of the data (from FIGS. 3 and 4) using an 80% correlation level. This clearly shows the detection of a single fibre of 200 μm in diameter at a depth of 75 mm when the fibre is filled with QUANTISON. The experiment is set up to simulate a triggered M-mode with the test object being a single fibre containing QUANTISON.

Figure 3:
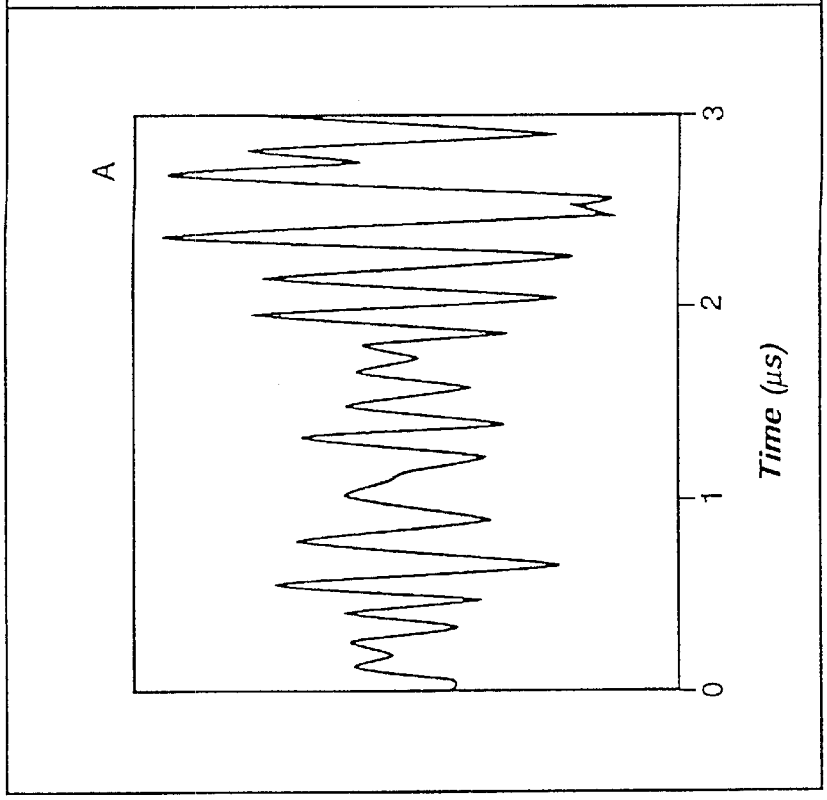
FIG. 3 shows an image resulting from an experiment with the first and third pulses without the power enhanced scattering effect produced by the second pulse.

FIG. 3 represents the result of the two Radio-Frequency (RF) imaging pulses without the high amplitude burst, in which no PES and no free air bubbles are detected.

Figure 4:
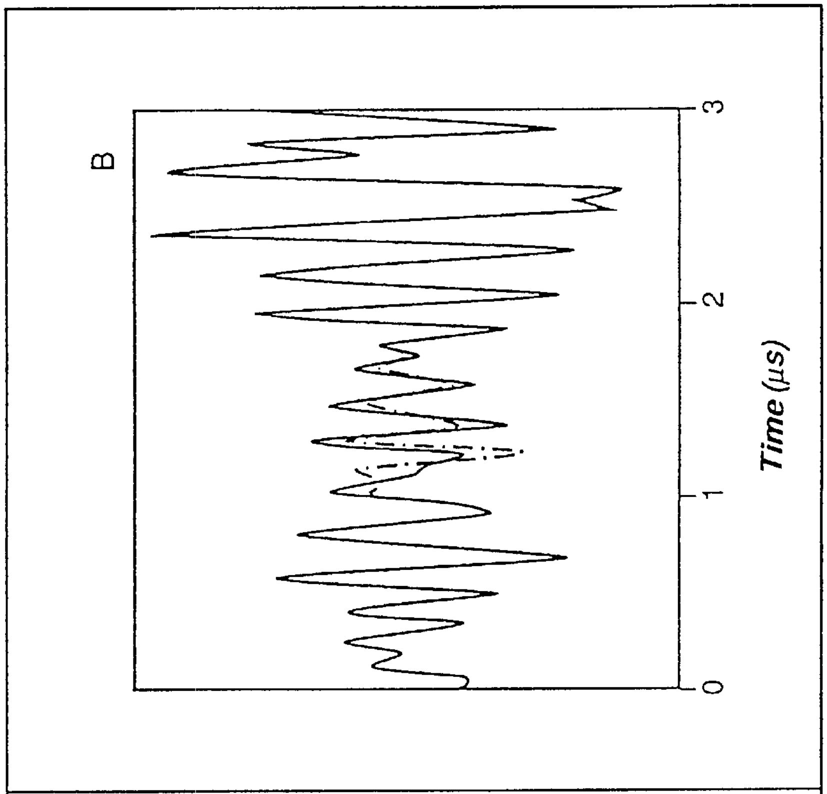
FIG. 4 shows the images resulting when all three pulses are present and with FIG. 2 shows the advantages of decorrelation.

FIG. 4 shows the result when the second burst, in between the image pulses, is switched on.

In this case, the second imaging pulse (the third pulse burst) detects the generated free air bubbles. The change in amplitude is minimal, due to the high scattering surrounding material. However, in combination with the 'comparison-based strategy', these minimal changes can be accurately detected.

The complete pulse sequence should be carried out within as short a period of time as is reasonably practical, bearing in mind the persistence of the evoked bubble release, acoustic velocities and depth of region of interest. In a particular example for the pulse sequence of FIG. 1, the total time period is 100 μs.

Other frequencies can be used for the first/third and the second pulse. For example, the first/third pulses can be 3 MHz and the second 500 kHz or the first/third pulses can be 5 MHz and the second 1 MHz.

The power of the first (10) and third (14) pulse bursts should be such as not to induce any power enhanced scattering (release of bubbles) from the QUANTISON. Thus the power of the first and thrid pulses should preferably not be higher than 0.1 MPa.

The power of the centre (second) pulse burst must be such as to produce power enhanced scattering as defined, and should preferably be above 0.6 MPa for QUANTISON.

The powers however could vary for other agents.

Because the frequency of the second pulse burst 12 is different from that of the first/third pulse bursts, it is convenient to filter out any residual effects from the second pulse burst when imaging.

This enables the third pulse burst to follow quickly on after or even overlap the second but as stated above, it is generally considered that the total sequence time, which could be as short as possible, will have to be a minimum of 100 μs for an object depth of 75 mm for most practical purposes. The total time could possibly be shorter if the imaged object was at a shallower depth.

Figure 5:
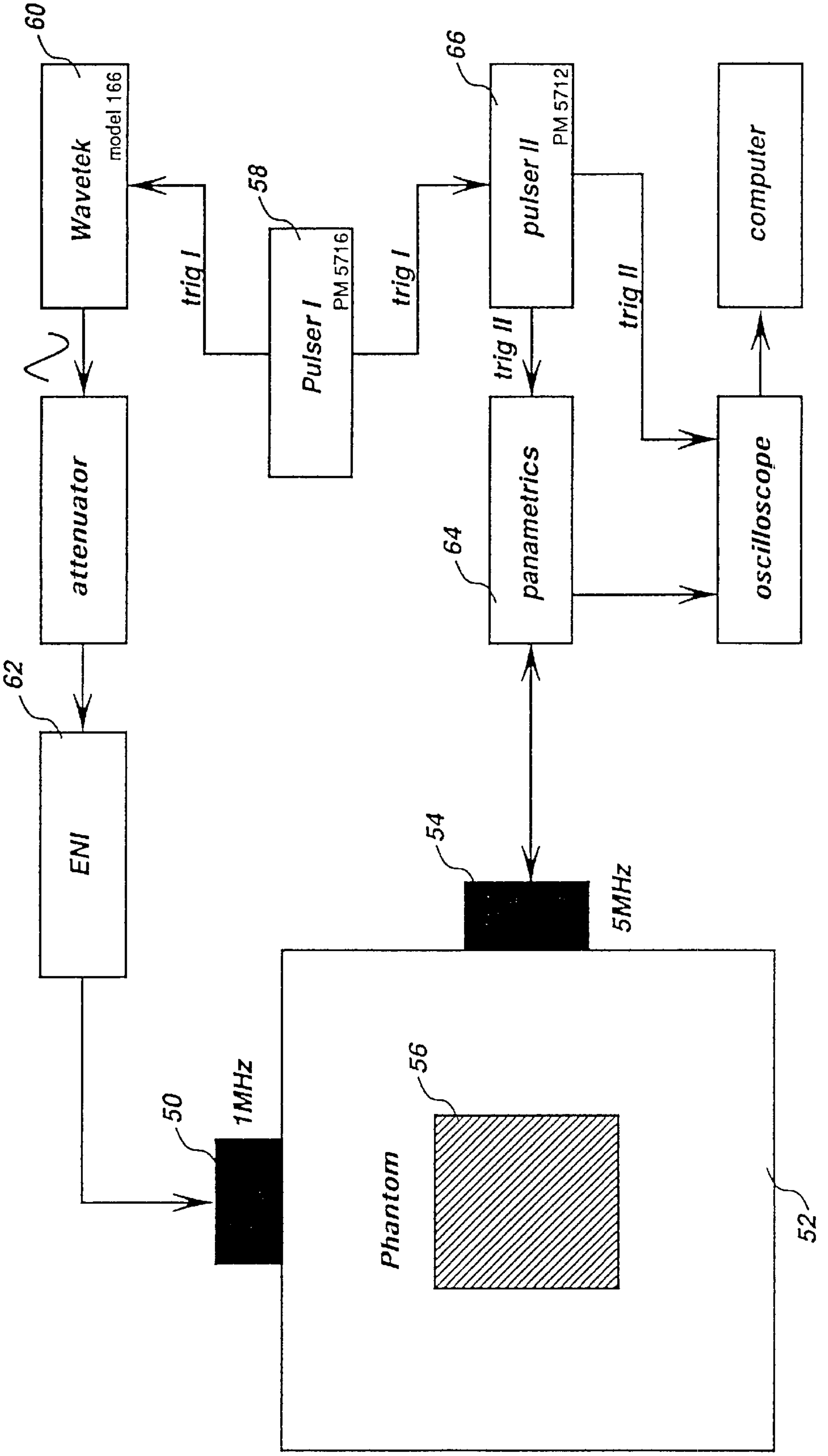
FIG. 5 shows a block diagram of a prior art apparatus.

Apparatus according to the prior art is illustrated in FIG. 5.

A 1 MHz single element transducer 50 (Panametrics, Waltham, Me., USA) with a focus at 7.5 cm is mounted in a water bath 52 filled with Isoton® II (Coulter Diagnostics) and used as the high power transmitter. Perpendicular to the acoustical beam of this transducer a 5 MHz single element broadband transducer 54 (Panametrics, Waltham, Me., USA), with a focus at 7.5 cm, is mounted and used to probe the target 56 positioned in the center of the waterbath (transmit/receive). The 1 MHz high power sinusoidal signal of 10 cycles with a peak-peak acoustical pressure of 1.8 MPa and repetition rate of 1 Hz is generated by a pulse generator 58 (PM5716, Philips) a Wavetek signal generator 60 and a linear power amplifier 62 model A500 (ENI, N.Y.). A short 5 MHz pulse is generated and received by apulser/receiver 64 (5052 PR, Panametrics, Waltham, Me., USA). The received signal can be amplified from +40 dB to −40 dB in steps of 2 dB. The amplified signal is filtered with a low pass Chebychev filter and digitized by a Lecroy 9400A (Lecroy, Chestnut Ridge, N.Y., USA) digital oscilloscope (100 MHz, 8 bits). The pulser/receiver is synchronized by a pulse generator 66 (PM 5712, Philips) with a delay of 0.5 ms relative to the 1 MHz transmitted signal. The output signals are recorded over time windows of 10 μs and transferred to a personal computer (Compaq 386/20e) for further analysis.

In an alternative embodiment the third pulse 12 could be combined within the second pulse since the scattered signal from the third pulse can be filtered out.

This will provide a shorter time period for the total experiment.

For other use, for example for velocity measurement, it is possible for the first and third pulses to be of relatively low frequency and for the second pulse to be of relatively higher frequency, i.e. the opposite of the first example.

Figure 6:
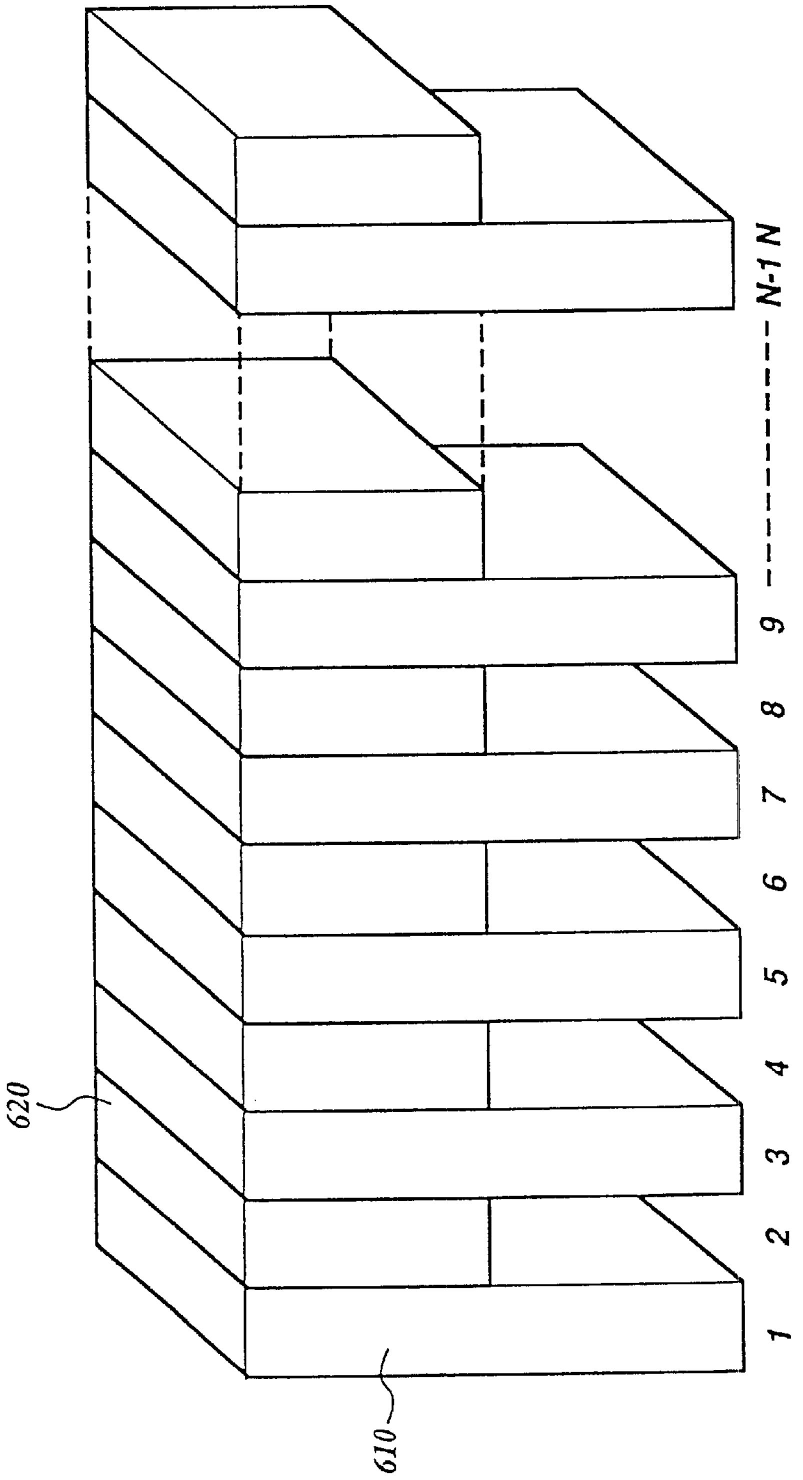
FIG. 6 shows a transducer.

With reference now to FIG. 6, a design of a transducer 600 with a frequency response suitable for the present invention is shown.

In this design two separate transducer elements 610, 620 are used. The first transducer element 610 is sensitive to low frequency and the second 620 is sensitive to high frequency. Both elements may be of the piezoelectric type.

The low frequency transducer (type 610) is used for sending, the other one 620 can be used for both receiving alone and for transmitting and receiving for imaging. For array transducers the two transducer types (610, 620) can be merged as shown by interleaving the two types, thereby defining e.g. the odd elements as type 1 and the even elements as type 2. Other distributions are also possible. Type 2 transducer can be used for imaging in both the fundamental as well as the second harmonic mode.

The above extensive description of the prior art leaves much to be desired relative to the physical construction of an ultrasound probe, comprising two interleaving sets of two types of transducer elements.

Object of the present invention is to provide an ultrasound probe that is simple in construction and can be used in ultrasound imaging using contrast enhancing agents.

An ultrasound probe according to the invention thereto is characterized in that said transducer elements of said first interleaved array are provided on a first, hollow, support member, in that said transducer elements of said second interleaved array are provided on a second support member, in that said second support member fits within said first support member, in that a length of said transducer elements of said first array in a plane of said array and in a direction substantially perpendicular to said longitudinal dimension is larger than a corresponding length of elements of said second array and in that said corresponding length of said transducer elements of said second array is not larger than a corresponding inside measure of said first, hollow, support member.

Thereby a sturdy and compact construction is achieved.

A preferred embodiment of an ultrasound probe according to the invention in which a single piece of backing material is connected to all second transducer elements is characterized in that an airgap is present between a backside of said first transducer elements and said backing material.

Thereby it is achieved that an amplitude of the ultrasound generated by the first transducer elements is larger than it would be when said first transducer elements would have been in contact with a backing.

Figure 7A:
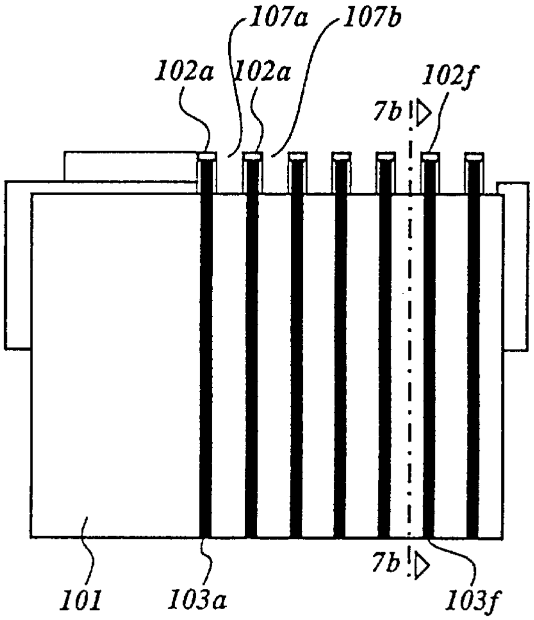
Figure 7B:
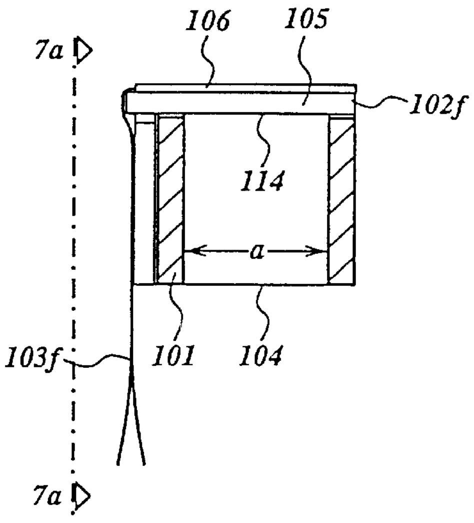
Figure 8A:
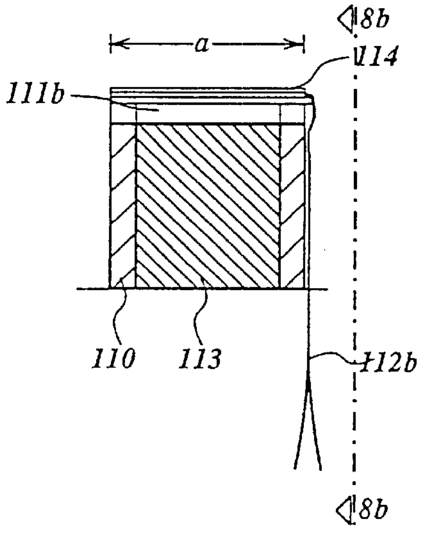
Figure 8B:
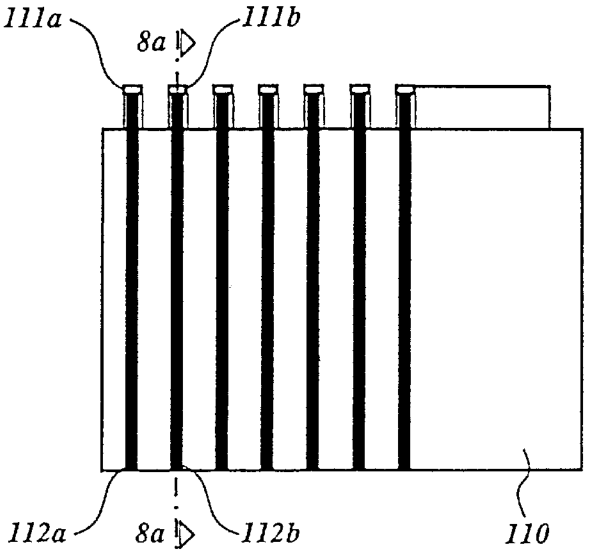
Figure 9A:
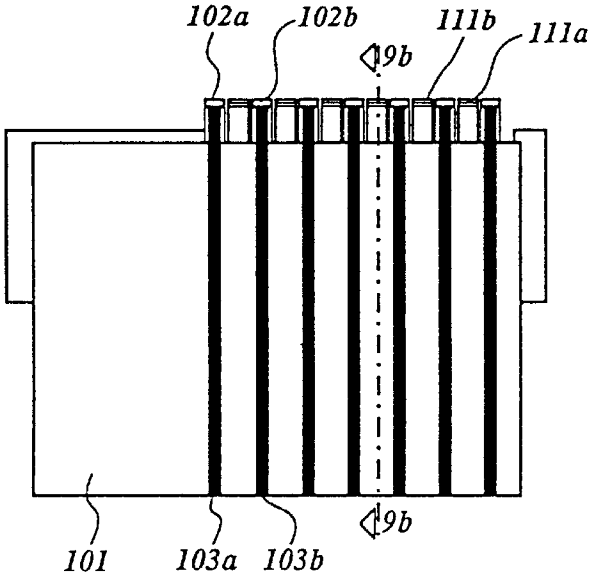
Figure 9B:
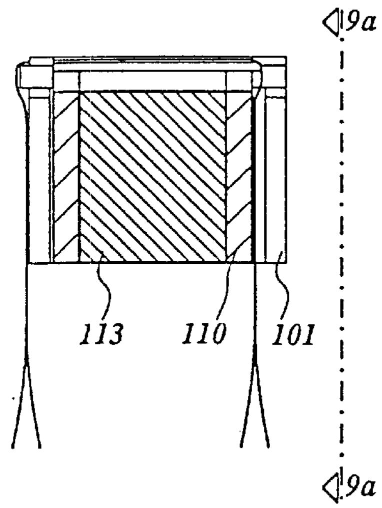
Figure 10:
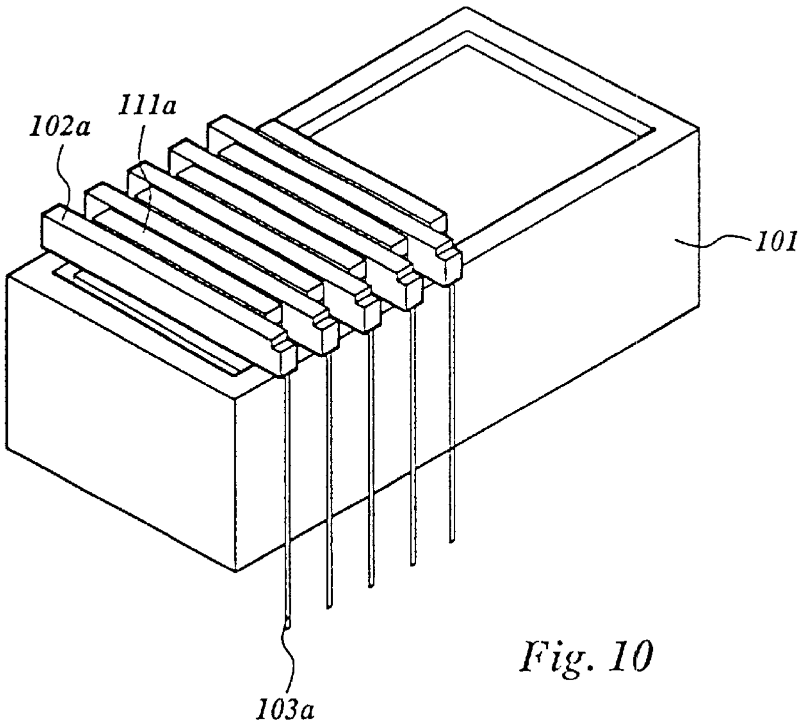

The invention will now be described with reference to the accompaning drawings in which FIG. 7A is a sideview of a first support element provided with first transducer elements and electrical contacts according to a view along lines 7*a*/7*a* shown in FIG. 7B;

FIG. 7B is a view along the lines 7*b*/7*b* in FIG. 7A;

FIG. 8A is a cross-sectional view along the lines 8*a*/8*a* in FIG. 8B;

FIG. 8B is a view along the lines 8*b*/8*b* in FIG. 8A and showing the second support element provided with second transducer elements and corresponding electrical contacts;

FIG. 9A is a view along the lines 9*a*/9*a* of FIG. 9B and showing a completed ultrasound porbe according to the invention;

FIG. 9B is a cross-sectional view along the lines 9*b*/9*b* in FIG. 9A;

FIG. 10 is a view of an ultrasound probe according to the invention.

FIG. 7A and 7B show a first support element 101 in the form of a rectangular box without a bottom and without a top. Across the top side of the support element 101 a number of transducer elements 102*a*, 102*b*, . . . , 102*f*, . . . is provided and fixedly connected to the support element 101. Each of the transducer elements is provided with a corresponding electrical contact 103*a*, . . . , 103*f*, . . . . The number of transducer elements 102 may be 48. The center frequency of each of the elements 102 is relatively low, for example 900 kHz. The transducer elements 102 are placed side by side, along a longitudinal direction of the first support element 101. A separation between subsequent first transducer elements is of the order of 250 μm, and the pitch of the array is 0.5 mm. Each individual transducer element 102 has its own individual connected ground-contact, for example by using flexprints 103 connected with conductive epoxy to the electrode of the transducer elements.

FIGS. 8A en 8B show the second array mounted on a second support element 110 and comprising transducer elements 111*a*, 111*b*, . . . is provided with electrical contacts 112*a*, 112*b*, . . . each of the transducer elements 111 is in contact with a backing 113. The backing 113 fills the entire innerspace of the second support element 110. Each of the transducer elements 111 is provided with suitable matching layers 114. The dimensions of the transducer elements 111 and of the matching layers 114 are such that the center frequency and the bandwidth of the transducer elements 111 comprise the second, third and fourth harmonic of the center frequency of the transducer elements 102 of the first array. As with the spacing between the elements 102 of the first array the spacing between the elements 111 of the second array is 250 μm and the pitch between subsequent elements is 0.5 mm. Also in this case each individual element has its own individually connected ground-contact, for example by using flexprints connected with conductive epoxy to the electrode of the transducer elements 111. It is also possible for the array to have one ground contact shared by all elements. Nevertheless in that case each element also has a contact for the second electrical contact for connection to a transmitting or receiving device. The pitches of the first array and of the second array are the same and their dimensions of the transducer elements 102 and 111 in the longitudinal direction of the arrays are such that the elements 111 fit neatly in the spaces 107 between the transducer elements 102 and the transducer elements 102 fit within the spaces between the transducer elements 111. FIGS. 9A, 9B and 10 show the ultrasound probe after the first and the second support elements have been integrated.

A bottom opening 104 of the first support elements 101 has been used for the passage of the second support element 110 into the inside of the first support element 101. Thereto the dimension b (see FIG. 8A) of the second support element is at most as large as an inner dimension a (see FIG. 7B) of first support element 101. After the second support element 110 has been inserted into the inside of the first supported element 101 both are firmly fixed together. As more clearly shown in FIG. 10 the elements 102 and the elements 111 form a single transmitting and receiving surface for ultrasound waves in a fully interleaved way of two separate arrays. The backing 113 for the element 111 of the second array does not fill the space between itself and a backside 114 of the transducer elements 102 of the first array.

The transducer elements 102 of the first array have a relatively low center frequency of for example 900 kHz. The bandwidth of the first array can be approximately 40 to 50%, which means that the bandwidth expressed in megahertz is about 40 to 50% of the centre frequency of 0.9 MHz. With respect to the first array the bandwidth is not or not very much important. However regarding the transducer elements 111 of the second array it is important that those elements are able to detect a higher harmonic, such as a second, a third or a fourth harmonic, of the center frequency used in the first array. This can for example be done by designing the thickness and the matching layers of the transducer elements 111 such that the center frequency is 2.8 MHz and the bandwidth is about 80%. The design of such transducer elements and corresponding matching, layers is no problem for a person skilled in the art and is not part of the present invention as such.

After the foregoing description other modifications and embodiments will become clear for the persons skilled in the art. Such modifications and embodiments are considered part of the present invention and covered by the following claims.

What is claimed is:

1. An ultrasound probe for ultrasound imaging using contrast enhancing agents comprising:

two interleaved arrays of transducer elements, each array having a longitudinal dimension along which transducer elements are placed side by side, a first interleaved array includes transducer elements having a lower center frequency and a second interleaved array including transducer elements having a higher center frequency, the transducer elements of the first interleaved array are provided on a hollow first support member, and the transducer elements of the second interleaved array are provided on a second support member, the second support member being adapted to fit within the hollow first support member, a length of transducer elements of the first array in a plane of the first array and in a direction substantially perpendicular to the longitudinal dimension is larger than a corresponding length of transducer elements of the second array, and the corresponding length of the transducer elements of the second array is not larger than a corresponding inside measure of the hollow first support member.

2. The ultrasound probe according to claim 1, wherein the hollow first support member is provided with electrical connections for first transducer elements thereon and the second support member is provided with electrical connections for second transducer elements thereon.

3. The ultrasound probe according to claim 1, wherein the hollow first support member further comprises a first opening covered by first transducer elements and at least one second opening having cross sectional dimensions capable of allowing access to an inside of the hollow first support member by the second support member provided with second transducer elements thereon.

4. The ultrasound probe according to claim 1, each of second transducer elements is provided with a backing.

5. The ultrasound probe according to claim 4, wherein spaces between the second transducer elements are filled with backing material.

6. The ultrasound probe according to claim 5, wherein a single piece of backing material is connected to all second transducer elements.

7. The ultrasound probe according to claim 4, wherein an airgap is present between a backside of first transducer elements and the backing material.

* * * * *